United States Patent
Biffinger et al.

(10) Patent No.: US 8,425,742 B2
(45) Date of Patent: Apr. 23, 2013

(54) HIGH-THROUGHPUT BIOLOGICAL SCREENING ASSAY USING VOLTAGE GRADIENTS

(75) Inventors: Justin C Biffinger, Woodbridge, VA (US); Meghann Ribbens, Los Angeles, CA (US); Kenneth H. Nealson, Los Angeles, CA (US); Bradley R Ringeisen, Lorton, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 635 days.

(21) Appl. No.: 12/683,988

(22) Filed: Jan. 7, 2010

(65) Prior Publication Data

US 2010/0176005 A1    Jul. 15, 2010

Related U.S. Application Data

(60) Provisional application No. 61/143,584, filed on Jan. 9, 2009.

(51) Int. Cl.
  *G01N 27/403* (2006.01)
  *H01M 8/16* (2006.01)
  *C12Q 1/00* (2006.01)

(52) U.S. Cl.
  USPC .......... 204/403.01; 429/401; 429/2; 435/243; 422/68.1; 422/82.01; 422/9.2; 205/777.5

(58) Field of Classification Search .................. 429/401, 429/2; 204/403.01–403.15; 205/777.5; 422/9.2, 422/68.1, 82.01; 435/243
  See application file for complete search history.

(56) References Cited

U.S. PATENT DOCUMENTS

2006/0024551 A1 * 2/2006 Smotkin .................. 429/34

OTHER PUBLICATIONS

Biffinger et al. (Biosensors and Bioelectronics 23 (2008) 820-826).*
Ringeisen et al. (Environ. Sci. Technol. 2006, 40, 2629-2634).*
Sittampalam et al. (Chemical Biology, 1997, 1:384-391).*
Penev et al. (Ecological engineering and environment protection, No. 1, 2008, pp. 74-81).*

* cited by examiner

*Primary Examiner* — J. Christopher Ball
*Assistant Examiner* — Jennifer Dieterle
(74) *Attorney, Agent, or Firm* — Amy L. Ressing; Stephen T. Hunnius

(57) ABSTRACT

A high throughput biological screening assay comprising at least two anodes, at least two cathodes acting as the reference electrode, and a polymer membrane placed between each anode and cathode, wherein the at least two anodes comprise a biological culture, and wherein the at least two cathodes comprise an oxidizing agent and a buffering agent. The high throughput biological screening assay wherein the at least two cathodes are connected in parallel to simulate the connection between the same cathode and different anodes. The high throughput biological screening assay further including an external resistor or open circuit and means for measuring the voltage across the external resistor or open circuit. A method of measuring power generation using a single cathode as a reference electrode to monitor the biological production of energy. A method of correlating bacterial biofilm formation within an operational microbial fuel cell directly to current output.

6 Claims, 6 Drawing Sheets

HIGH-THROUGHPUT BIOLOGICAL SCREENING ASSAY USING VOLTAGE GRADIENTS

This application is a non-provisional application of and claims priority to U.S. patent application No. 61/143,584 filed Jan. 9, 2009, the entirety of which is herein incorporated by reference.

The most time consuming part of environmental bacterial sampling or functional genomic screening is not the molecular biology of the system, but the cell biology and/or screening procedures used for analysis.

This screening is crucial as the best candidate mutants or species for a given application need to be identified quickly and accurately. High-throughput screening (HTS) continues to be primarily focused on assay technology (automation, detection, and miniaturization). Little to no effort has been put forward to analyze electrochemically active biological species that could be used for energy harvesting devices such as biological fuel cells.

Biological fuel cells offer a clean, renewable and potentially autonomous source of energy in the same vein as other environmental power sources such as solar, geothermal, and wind. Biological fuel cells can be separated into two classes.

One class is termed enzymatic because they utilize isolated immobilized enzymes to deliver reducing equivalents to the electrode surface but usually require redox mediators to facilitate electron transfer.

The second class of biological fuel cells is named microbial fuel cells (MFC). MFCs rely upon the metabolic cycle of living bacteria to generate electrons that are then harvested by the anode and transferred to the cathode where a complementing reduction reaction occurs.

The technology involved in biological fuel cells is scalable (anode, cathode, fluidic chambers, microbe attachment to anode, etc.) and could potentially be used in both real-time aquatic and terrestrial applications.

However, the isolation and identification of thousands of bacterial species and their mutants or the activity of millions of enzymes with a wide variety of substrates is a difficult and time consuming process with little to no standardization between one species and the next.

This disclosure describes fabricated miniature batch fuel cells (MBFC).

One embodiment includes the MBFC being made from 1 mL pipettes and Nafion® membranes.

Further, this disclosure describes a high throughput microbial testing assay.

One embodiment includes using the metal reducing microbe, *Shewanella oneidensis*.

The MBFC array operates by producing continuous power for days using a common catholyte and cathode but separate anodes, high throughput screening of different electron producing elements.

If the bacteria or enzymes are to be compared in an assay, it is important that a single electrode behaves like a reference electrode in the system, i.e. that the performance of the cathode from one test to another does not vary. It is important that this electrode is invariant so that changes in performance can be determined to be based entirely on the array performance, and therefore the performance of the biological species being tested.

In one embodiment of the invention described herein it could comprise at least 8 and up to 96 wells. Each chamber can optionally be assayed in multiple well devices simultaneously. For example, multi port battery test station or programmable load bank with voltage dependent data collection, a device station that can engage more than one multi-well device, or separate data collection stations, to increase high-throughput capacity.

The high throughput nature of this invention and fundamentals behind the design are key to the potential to rapidly survey hundreds to thousands of biological mutants and enzymes for power generating potential and decreasing the overall cost of isolating and identifying bioelectrochemically active catalysts for energy harvesting devices.

In addition, there are important commercial applications for methods to identify and isolate power generating biological catalysts (enzymes and microbes). Specifically, developing such a high throughput screening method would represent a substantial advance in the field of biological energy harvesting technology.

Methodologies are needed to more rapidly screen microbial mutants or enzymes that yield advantageous catalytic properties such as use of fuel, higher efficiency, more electrons generated, etc. This would allow for the elimination of unsuitable compounds and genomic mutation series from further development efforts, and also give the investigator insight as to the nature of metabolites, biofilm formation, and expression of proteins, with potential biological activity derived from certain fuels.

The rapid identification of mutants or enzymes engineered for power production will ultimately have substantial applications, primarily as a method to enhance the power production capabilities of biological fuel cells. These power sources have relevant applications, primarily as a long-term energy harvesting mechanism to power MEMs/NEMs sensor networks for chemical, biological or acoustic stand-off detection.

This rapid screening technology for biological energy harvesting catalysts would be beneficial to both enzymatic and microbial energy harvesting devices.

This disclosure describes a high throughput screening assay for bioelectrochemically active enzymes and microbes Other applications include enhancing power production from microbial power sources by utilizing genetic mutants determined to be acclimated for generating current or using a certain fuel or a biological sensor grid for chem/bio detection using changes in voltage output for detection.

Another application includes Sewage Treatment Plants—several applications including the ability to scrub or reduce biological oxygen demand and use metal reducing bacteria to produce power from a fuel cell using bacterial species or consortia and/or enzymatic catalysis determined beneficial through voltage output from a high throughput device.

Furthermore, disclosed herein are mixtures of high throughput sensors that rapidly determine the optimal configuration for designing both the anode and cathode for biological fuel cells simultaneously as well as changes in cellular physiology in an operational biological fuel cell.

Still furthermore, this disclosure can be used for enhancing power production from enzyme power sources by testing various enzyme/electrode assemblies and their ability to efficiently transfer electrons.

EXAMPLE

A third 1 mL pipet microbial fuel cell (MFC 1) was added to the same 75 mM ferricyanide catholyte as the previous two 1 mL pipet microbial fuel cells (MFCs 2 and 3) already running. All the cathodes were connected by a titanium wire and then connected externally in a parallel circuit. Power curves were recorded for each MFC with no significant variation in the power generating characteristics. MFC2 did produce more current than MFCs 1 and 3 but it was determined to be a variation on how the cathode was connected with the titanium wire. The single cathode with independent anodes is a concept that will work for making a high throughput device based off of these results.

Figure 1A:
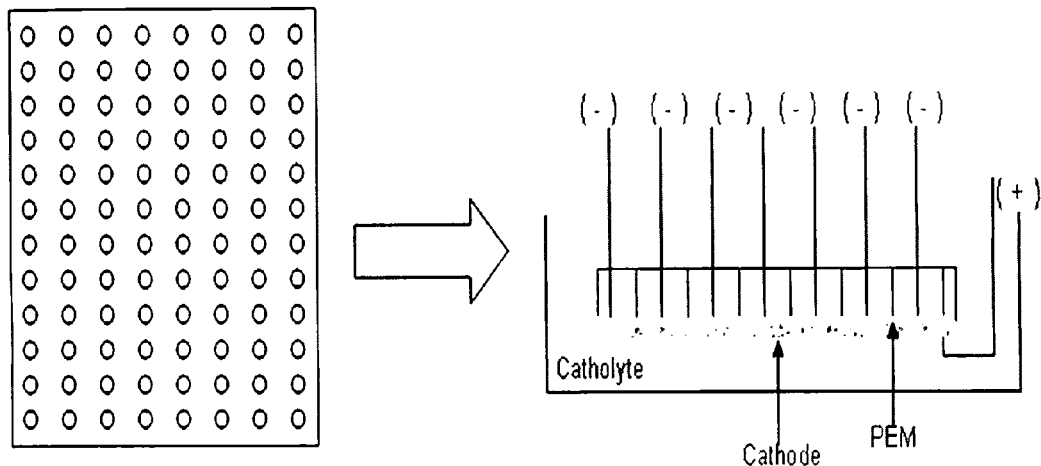
FIG. 1A is a schematic representation of a 96-well design HTS assay for power production.

The rapid screening of biological consortia or single species will reduce the time and cost of full scale electrochemical characterization of power producing species, a significant increase in the amount of platforms for enzymatic immobilization or microbial biofilm formation on solid supports, and functional miniaturization of biological fuel cells (the integration of micro-assay elements in a format compatible with robots and standard fluid handling tools) would be three unique features demonstrated by using this invention.

Therefore, these multi-well high-throughput assays will be able to monitor activation or inhibition of the enzyme cascade inside living whole cells or isolated enzymes using the voltage gradients generated by each species.

If biological fuel cells are to be used in the energy harvesting applications they are slated for then ability to screen bacteria and their genetic mutants along with a cascade of enzymes will be important.

Using plate technology and integrating it with fuel cell progress will lead to new libraries of biological catalysts that are capable of generating current in a fuel cell device.

Several strategies have been used for the high-throughput screening of both whole cell or enzymatic catalytic activity and function. After the introduction of the 96-well microtiter plate and spectrophotometric plate readers, a clear distinction arose between high-throughput screening and traditional laboratory assays. Some of these differences are provided in Table 1.

The significant differences between laboratory assays and HTS would be the size of the sample is significantly smaller for HTS, the protocol for HTS needs to be simple, and reagents are only added to the chamber. There are no high-throughput assays to monitor biological function as it relates directly to power production. The basic system setup for microbial fuel cells can be applied directly to HTS technology to create μL batch reactors for both enzymatic or microbial power production.

TABLE I

| Parameter | Laboratory | HTS |
|---|---|---|
| Protocol | Maybe complex with numerous steps | Less than 10 steps, simple, addition only |
| Assay volume | 0.1 mL-1 mL | <1 μL-100 μL |
| Reagents | Quantity often limited, different batches | Single batch, stable over long time |
| Variable | Many, time, substrate, compound | Compound (mg quantity), compound concentration |
| Assay container | Tube, slide, microtiter plate, Petri dish, cuvette, animal | Microtiter plate |
| Time | Milliseconds-months | Minutes-hours |
| Output | Plate reader, size separation, radioactivity | Plate reader (fluorescence, luminescence, absorbance) |

To date, the screening of enzymes and microbes for power production has been laboratory specific with no clear device that would quickly determine the utility of one catalyst versus the next. Many laboratories relate metal reduction by microbes as being a signifier for use in microbial fuel cells. However, this is not the case with several bacterial species never showing promise within energy harvesting devices but still reduce iron, chromium, and manganese salts. There is work on a rapid screening routine for identifying Mn(IV) or Tc(VII) reduction by *Shewanella* mutants using plate assays. As a result, the growth conditions for the assays are identical on each agar plate and only 10-12 colonies could be analyzed by digitally imaging each plate separately.

The proposed multi-well device in this application will use voltage as a detection method and will be able to maintain different growth conditions in the same assay. There is already a mini-bioreactor that can create twenty four different growth conditions for a microbe by changing the pH. $O_2/CO_2$ content, and temperature, but only recently has the change in dissolved oxygen content been used to monitor the in situ growth of *E. coli* within a multi-chamber device.

The proposed invention will be able to monitor current production as it relates to cell growth and biofilm formation.

Figure 1B:
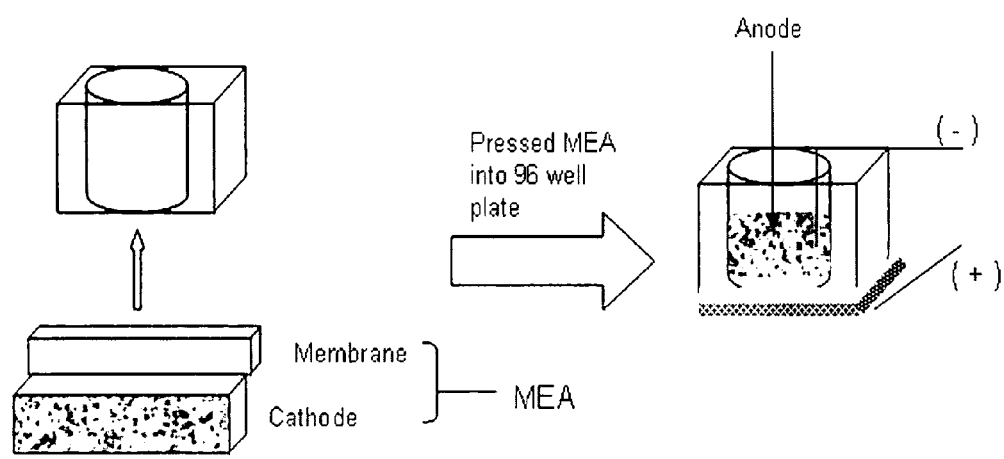
FIG. 1B is a fundamental design of one well for a 96-well HTS assay for bioelectrochemical activity.

The search for better fuel cell catalysts have lead some researchers to explore high-throughput screening methods for hydrogen or methanol polymer electrolyte membrane (PEM) fuel cells. Unlike these high temperature fuel cells, biological fuel cells do not require the stringent catalyst preparation; thus making it possible to create a biological batch reactor with a common cathode and catholyte directly from plate technology (FIG. 1A). FIG. 1B shows how a partially formed membrane electrode assembly could be used to create the 96-well form of this device.

Conditioning of the anode surface is not a spontaneous process considering bacterial biofilm formation can take place over a matter of years and so this invention will allow for longer time periods for data collection and potentially easy integration with scanning electron microscopy to evaluate biofilm formation. In addition, interaction between microbes and solid electrode surfaces will result in complex microbial physiological changes that cannot be monitored in real time with current microbial fuel cell technology.

The use of enzymes would better be suited for immediate power production considering they would be immobilized prior to the start of the assay on the conductive anode support. Enzyme immobilization is a very active field of research and this invention would contribute significantly to the expansion of enzyme-based fuel cells as well.

Example

Figure 2:
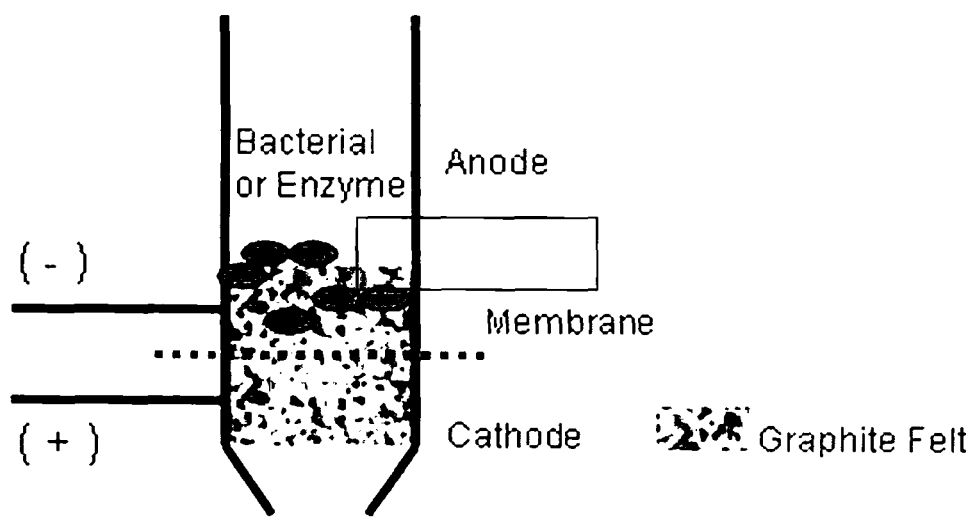
FIG. 2 is a design of a single pipet biological fuel cell.

This example concerns the goal of demonstrating the basic principles to creating and fabricating a HTS assay for bioelectrochemically active species using a single reference electrode. An image of the basic design of one of the pipette fuel cells is shown in FIG. 2. It consists of a 1 mL pipette tip (6 cm total size) cut into two pieces 2 cm from the bottom of the pipette. Graphite felt (15 mg) was connected with a titanium wire and placed inside the bottom chamber (cathode) of the pipette. Holes were punched into the side of the cathode chamber to ensure a good connection with the catholyte. A Nafion-117 membrane was placed in between the two chambers and sealed with 5 minute epoxy and then sealed with marine epoxy along the outside of the device. A separate pipet was used to add 600 µL of a culture of Shewanella oneidensis DSP 10 in Luria-Bertani ($1\times10^8$ CFU/mL) to the upper chamber (anode). After the bacteria were added, 25 mg of graphite felt (connected with a titanium wire) was pressed into the anode chamber. The pipette fuel cell was submerged into a solution of 75 mM potassium ferricyanide in 100 mM phosphate buffer (pH 7) over the seal made by the Nafion membrane and marine epoxy. Sodium lactate was periodically added to the anode to concentrations of 20-30 mM over the period of 4-6 days.

Figure 3:
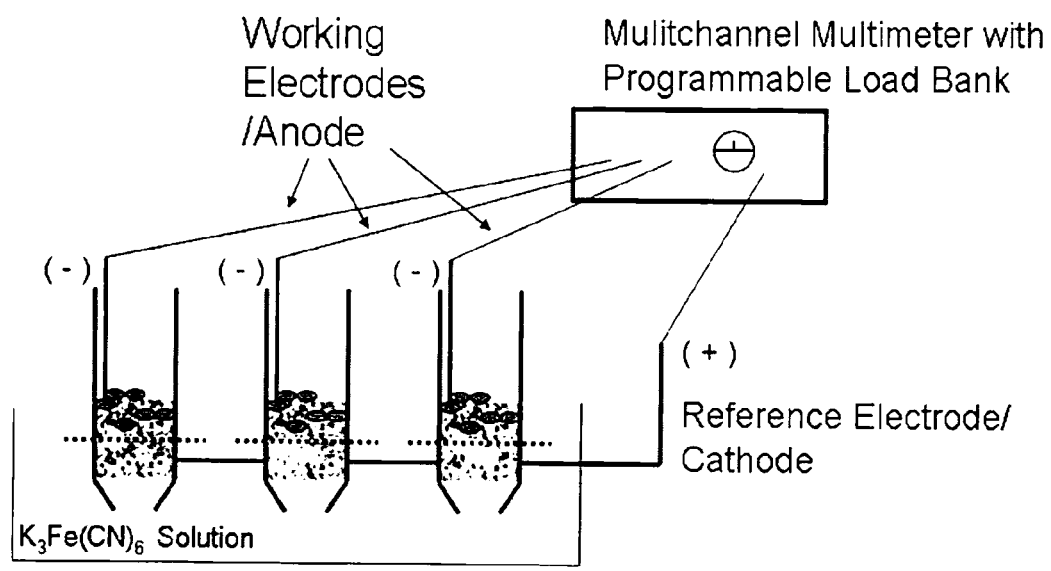
FIG. 3 is a reactor setup for multiple monitoring of pipet fuel cell data.

Over the time course of the experiment three similar fuel cells were fabricated and added to the same ferricyanide solution (FIG. 3). The ferricyanide solution (75 mM in 100 mM phosphate buffer (pH 7.2)) was used as the reference electrode in the system. The cathodes were connected in parallel with a wire to simulate the connection between the same cathode and different anodes. The large excess of ferricyanide assured that over the time course of the experiment the cathode potential would not change. To ensure proper mixing, the catholyte was stirred with a magnetic stir bar and to avoid localized diffusion gradient limitations.

Figure 4:
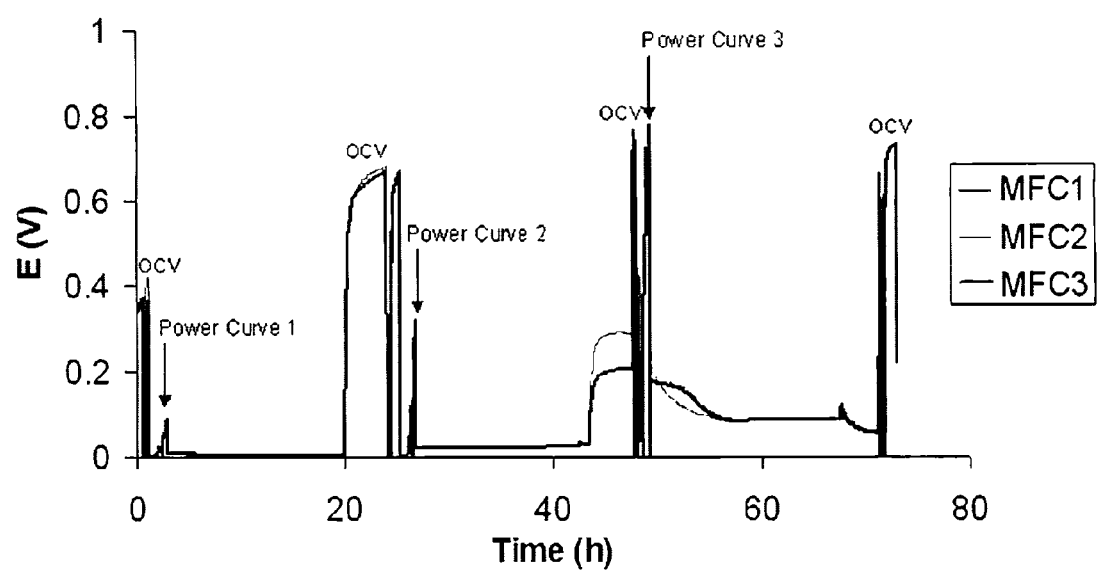
FIG. 4 illustrates time dependent data from all three one mL pipet fuel cells with connected cathodes. OCV: Open circuit voltage.

The anode was comprised of a S. oneidensis culture (3 days old) in Luria-Bertani broth. The voltage across an external resistor (8600Ω) or at open circuit (OC) was recorded with a PersonalDAQ/54 data acquisition system (I/O Tech/Cleveland. Ohio). The time dependent data from the three pipet batch fuel cells are provided in FIG. 4. The difference in voltage output between MFCs 1 and 3 under identical conditions was negligible while MFC 2 exhibited a slight variation from the other two. Proper fabrication of electrodes for use in this device (pressed carbon electrode or carbon paper electrodes connected with titanium wires for the anode and cathode, respectively) will eliminate any variation between each chamber of a HTS device.

Figure 5:
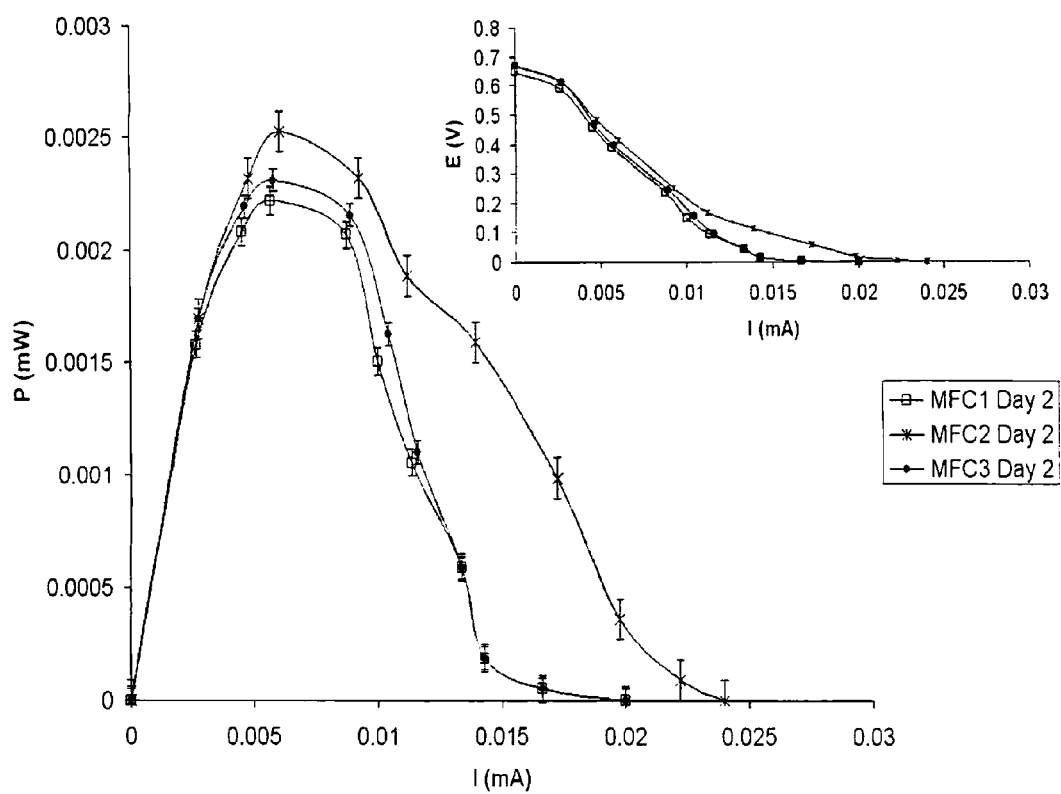
FIG. 5 illustrates polarization curves recorded from each one milliliter pipet fuel microbial batch reactor after 40 hours of operation.

The difference between MFCs 1/3 and MFC 2 was also observed when polarization curves were recorded from each device, FIG. 5.

The polarization curves for each pipette fuel cell were recorded by changing the external resistance of each fuel cell independently. For a HTS setup, a programmable load bank with at least 96 ports for data collection can be used to monitor both power and voltage with time of each chamber simultaneously. Also, the anode electrode could be standardized by either separate fabrication or better machinability. Overall, even with variation that were most likely due to inconsistent fabricated methods and the high sensitivity of voltage measurements, these power outputs for three separate fuel cells had a standard deviation of 10%.

The invention disclosed herein capitalizes on the concept that power generation can be monitored using a single cathode as a reference/counter electrode to monitor the biological production of energy in a high throughput design.

A system using three pipet tip microbial fuel cells demonstrated this design with the largest variation between the fuel cells being 10%. Inconsistent fabrication of electrodes, and the high sensitivity of this measurement, created the slight discrepancy in the results. Additional designs convert this laboratory prototype 3-chamber device into a high throughput assay (at least 96-well plate).

Figure 6:
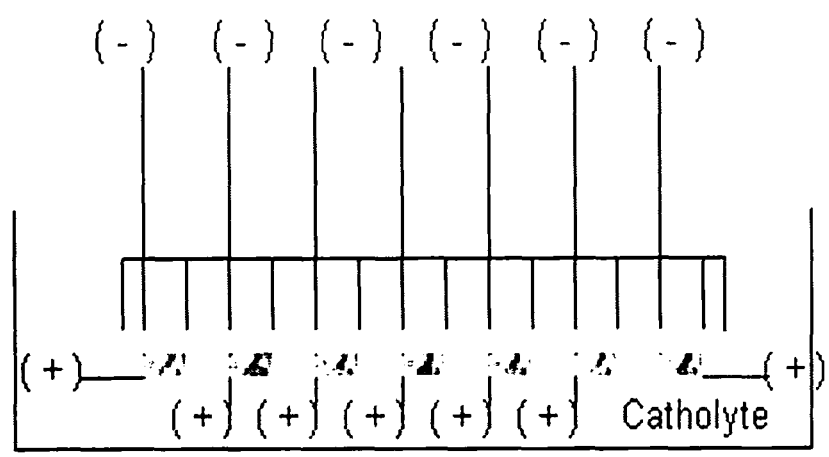
FIG. 6 is a design for high-throughput array for both cathode and anode variation This disclosure describes an apparatus and method to provide a high-throughput scalable electrochemical assay device based on biological metabolic function that includes at least three unique features and a single counter/reference electrode.

This is a very important advance considering the need to determine the properties of both bacterial consortia or single strains for use in energy harvesting devices or sensors. The proposed use of this design is geared toward a high-throughput screening assay for bioelectrochemically active species (both enzymatic and whole cell) like FIG. 1A and FIG. 6.

To date, there are no high throughput screening assays that use the voltage gradients generated by biological catalyst of interest to determine the power generating capabilities of a species or protein.

Traditional methods would require large fuel cells to be assembled to test each species. Each traditional test (large-scale fuel cell) could require weeks to months, and testing hundreds of species would require almost insurmountable amounts of time, effort and supplies.

This disclosed miniaturized, high throughput approach will enable the facile screening of hundreds to thousands of candidate biological catalysts.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g. using the articles "a," "an," "the," or "said" is not construed as limiting the element to the singular.

What is claimed is:

1. A high throughput biological screening device comprising:
    at least two fuel cells;
    wherein each of the at least two fuel cells comprises an anode chamber, a cathode chamber and a polymer membrane placed between the anode chamber and the cathode chamber;
    wherein the at least two cathode chambers each comprise a cathode, an oxidizing agent and a buffering agent;
    wherein the at least two anode chambers each comprise an anode and a biological culture; and
    wherein the at least two cathode chambers are connected in series with a wire and configured to function as a single reference electrode versus each individual anode chamber.

2. The high throughput biological screening assay of claim 1 further including an external resistor or open circuit and means for measuring the voltage across the external resistor or the open circuit.

3. The high throughput biological screening assay of claim 2 wherein the oxidizing agent is potassium ferricyanide.

4. The high throughput biological screening assay of claim 1 wherein the at least two anodes consist of pressed carbon or conducting support coated with carbon and the at least two cathodes consist of carbon paper.

5. The high throughput screening assay of claim 4 wherein Shewanella oneidensis DSP10 in Luria-Bertani ($1\times10^8$ CFU/mL) is the biological culture.

6. A method of correlating bacterial biofilm formation within an operational microbial fuel cell directly to current output comprising;
    utilizing the high throughput device of claim 1; and
    detecting the voltage gradients generated by the biological cultures.

* * * * *